(12) United States Patent
Richards et al.

(10) Patent No.: US 6,472,217 B1
(45) Date of Patent: *Oct. 29, 2002

(54) SLIDE AQUEOUS VOLUME CONTROLLING APPARATUS

(75) Inventors: William L. Richards, Tucson, AZ (US); Devon C. Campbell, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/415,030

(22) Filed: Oct. 7, 1999

Related U.S. Application Data

(63) Continuation-in-part of application No. 07/488,601, filed on Mar. 2, 1990, now abandoned, and a continuation-in-part of application No. 07/924,052, filed as application No. PCT/US91/01149 on Feb. 28, 1991, now abandoned, and a continuation-in-part of application No. 08/352,966, filed on Dec. 4, 1994, now Pat. No. 5,595,707, and a continuation-in-part of application No. 08/469,527, filed on Jun. 6, 1995, now Pat. No. 5,650,327, and a continuation-in-part of application No. 08/906,678, filed on Aug. 5, 1997, now abandoned.

(51) Int. Cl.$^7$ .................................................. G01N 1/38
(52) U.S. Cl. ........................ 436/46; 436/43; 436/174; 436/180; 422/63; 422/64; 422/100; 118/416; 118/425
(58) Field of Search ............................ 422/63, 64, 67, 422/100, 104; 436/46, 49, 45, 174, 180; 141/130, 145; 118/416, 425; 435/40.5

(56) References Cited

U.S. PATENT DOCUMENTS

| | | | |
|---|---|---|---|
| 3,932,683 A | * 1/1976 | Robins et al. ................. | 118/63 |
| 4,335,673 A | * 6/1982 | Fixot ........................... | 118/401 |
| 5,009,185 A | * 4/1991 | Stokes et al. ................ | 118/314 |
| 5,225,325 A | * 7/1993 | Miller et al. .................... | 435/6 |
| 5,425,918 A | * 6/1995 | Healey et al. ................ | 422/64 |
| 5,439,649 A | * 8/1995 | Tseung et al. ................ | 422/99 |
| 5,645,114 A | * 7/1997 | Bogen et al. ................ | 141/145 |
| 5,654,199 A | * 8/1997 | Copeland et al. ........... | 422/100 |
| 6,093,574 A | * 7/2000 | Druyor-Sanchez et al. . | 436/180 |

FOREIGN PATENT DOCUMENTS

WO    WO91/13335    * 9/1991

* cited by examiner

Primary Examiner—Jill Warden
Assistant Examiner—Kathryn Bex
(74) Attorney, Agent, or Firm—McDonnell Boehnen Hulbert & Berghoff

(57) ABSTRACT

Apparatus and methods for controlling the fluid on a slide are provided. Fluid reduction is accomplished by directing stream(s) of fluid at an edge of the slide, the streams of fluid being at an angle with the slide of less than 90°. The surface tension at the edge of the slide is broken by the stream(s). And, the fluid which is on the slide is drawn or pulled by the streams of liquid, thereby reducing the fluid on the slide to a reproducible, consistent level.

13 Claims, 5 Drawing Sheets

SLIDE AQUEOUS VOLUME CONTROLLING APPARATUS

CROSS REFERENCE TO RELATED APPLICATIONS

This application is a continuation in part of U.S. patent application Ser. No. 07/488,601 (now abandoned), filed Mar. 2, 1990; a continuation in part of U.S. application Ser. No. 07/924,052 (now abandoned), filed Aug. 31, 1992 which is the U.S. national phase application of International Application No. PCT/US91/01149, filed Feb. 28, 1991, published as WO91/13335, Sep. 5, 1991; a continuation in part of U.S. application Ser. No. 08/352,966, filed on Dec. 4, 1994 (issued as U.S. Pat. No. 5,595,707); a continuation in part of U.S. application Ser. No. 08/469,577 filed on Jun. 6, 1995 (issued as U.S. Pat. No. 5,650,327); and a continuation in part of U.S. application Ser. No. 08/906,678 filed on Aug. 5, 1997 now abandoned. This application incorporates by reference the entire subject matter of U.S. application Ser. Nos. 08/352,966, 08/469,577 and 08/906,678.

BACKGROUND OF THE INVENTION

The present invention relates to an automated biological apparatus and, more particularly to a method and apparatus for rinsing a biological sample on a slide.

Processing of biological samples, such as immunohistochemical staining, typically occurs by placing the biological sample on a standard slide. The slides are placed in a staining machine, such as the machine disclosed in U.S. application Ser. No. 08/995,052 filed on Dec. 19, 1997, which is hereby incorporated by reference in its entirety. An important feature in the processing is the control of the amount of liquid on the slide. During processing, a specific, predetermined amount of liquid on a biological sample is typically desired. However, prior art methods of rinsing or removing the amount of liquid on the slide are inaccurate in the control of the amount of fluid on the slide, have the possibility of disrupting the sample on the slide and/or are complicated in their mechanics. One such method includes sending a stream of liquid from one end of the slide to the other end of the slide via a volume controlling device (i.e., "pushing" the liquid off of the slide). Specifically, the volume controlling device sends streams or jets of liquid onto the section of the slide proximate to the volume controlling device so that the rinse liquid passes over the portion of the slide where the biological sample is placed and off of the distal end. In this manner, the stream of liquid "pushes" the liquid off of the slide. This method, however, may disrupt the biological sample due to the passing of fluid over the biological sample.

Another method to control the amount of fluid on a slide is by rotating the slide so that the liquid runs off by gravity. This method uses a slide holder that allows the rotation of the slide and an air cylinder that pushes a tab on the holder to make it rotate and "tip" the slide over, thus permitting the aqueous to drain off. However, the mechanics required for rotation of the slide may be complicated. Accordingly, it is desirable to have an improved method and apparatus to control the amount of fluid on the top of a slide.

SUMMARY OF THE INVENTION

The present invention is directed to apparatus and methods for processing tissue samples mounted on microscope slides. In a first aspect of the invention, a method for rinsing a slide having a biological sample positioned on an upper surface of the slide is disclosed. The method comprises the steps of applying a layer of fluid onto the upper surface of the slide so as to cover the biological sample with fluid, and removing at least a portion of the fluid applied onto the upper surface by pulling the fluid from the slide.

In a second aspect of the invention, a method for rinsing a slide having a biological sample positioned on an upper surface thereof is disclosed. The method comprises the steps of applying a layer of liquid onto the upper surface of the slide so as to cover the biological sample with the liquid and directing at least one stream of fluid in between the biological sample and an end of the slide so as to reduce to amount of fluid on the upper surface of the slide, the at least one stream of the fluid making an angle with the slide of less than 90°.

In a third aspect of the invention, an automated biological reaction apparatus is disclosed. The apparatus comprises a controller including a processor and a memory device in communication with the processor, a volume controlling device including means for applying fluid onto a slide, the means for applying fluid onto the slide being in communication with the processor and means for pulling the fluid from the slide, the means for pulling the fluid from the slide being in communication with the processor.

In a third aspect of the invention, an automated biological reaction apparatus is disclosed. The apparatus comprises a controller including a processor and a memory device in communication with the processor, a volume controlling device including compressor, at least one container containing fluid, the container being connected to the compressor via a pressure line, at least one valve connected to the container, the at least one valve in communication with the processor, fluid reducing device connected to the at least one valve and positioned above a slide, the fluid reducing device having at least one nozzle outlet for directing at least one stream of fluid between a biological sample and an edge of the slide, the stream of fluid making an angle of less than 90° with the slide.

It is an advantage of the present invention to provide a method and apparatus for controlling the amount of fluid on a slide.

It is still an advantage of the present invention to provide a method and apparatus for drawing or pulling the fluid off the slide rather than pushing or blowing it off.

It is another advantage of the present invention to provide a method and apparatus for having a controlled process that is minimally disruptive to the tissue and the tissue environment on the slide.

It is a further advantage of the present invention to provide a method and apparatus for breaking the surface tension at an end of the slide.

It is still a further advantage of the present invention to provide a method and apparatus for pulling of liquid off of an end of the slide.

With the foregoing and other objects, advantages and features of the invention that will become hereinafter apparent, the nature of the invention may be more clearly understood by reference to the following detailed description of the invention, the appended claims and to the several views illustrated in the drawings.

BRIEF DESCRIPTION OF THE DRAWINGS

FIG. 2b is an expanded perspective view of the nozzles of the fluid reducing device in FIG. 2a.

DETAILED DESCRIPTION OF THE PRESENTLY PREFERRED EMBODIMENTS

Figure 1:
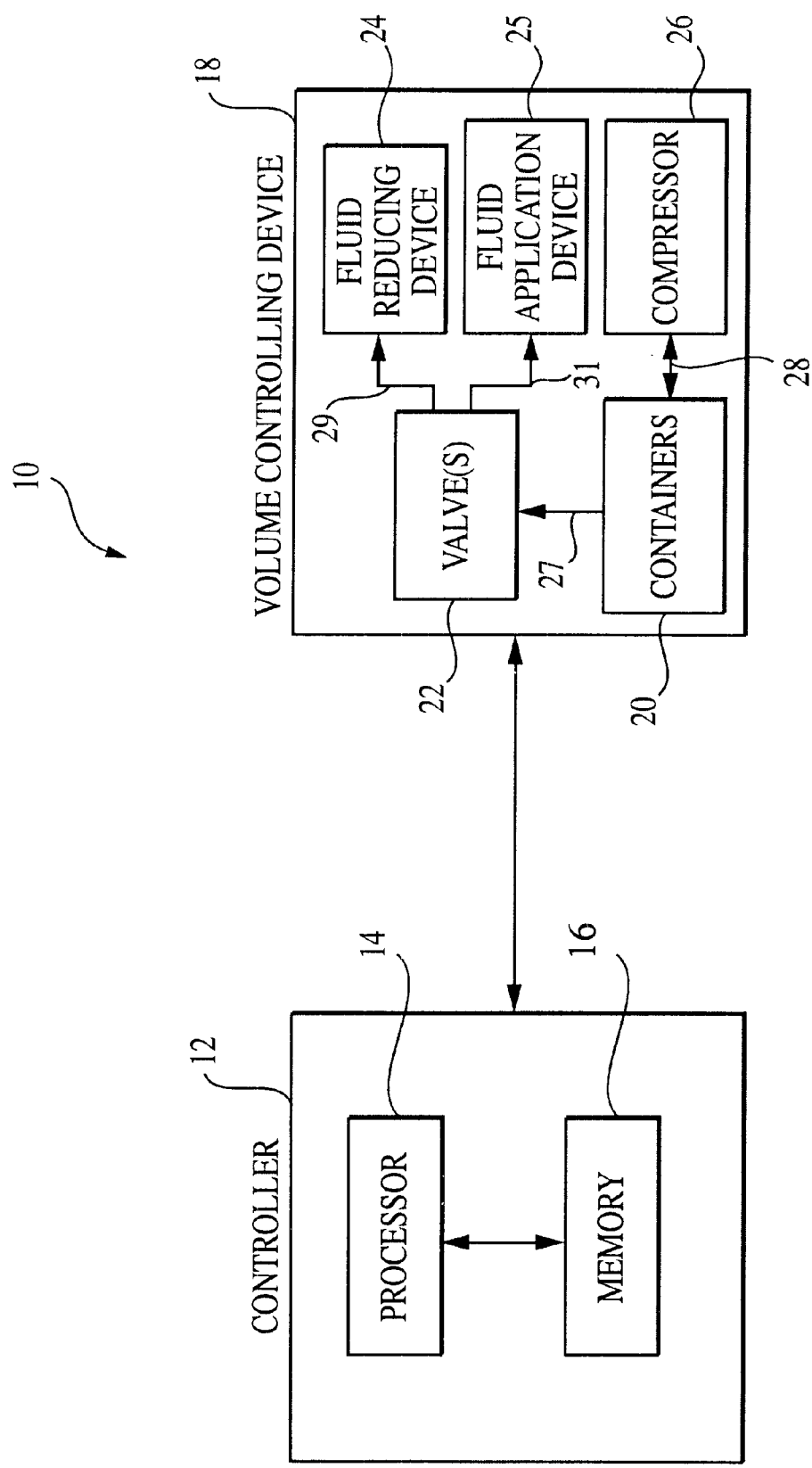
FIG. 1 is a block diagram of a rinsing subsystem of a staining device.

Referring now in detail to the drawings wherein like parts are designated by like reference numerals throughout, there is illustrated in FIG. 1 a block diagram of a volume control subsystem 10 of a staining device. The staining device includes a controller 12, which in a preferred embodiment, is a microcontroller. The controller 12 includes a processor 14 and a memory device 16. The memory device may either be a volatile memory (such as Random Access Memory) or non-volatile memory (such as Read Only Memory). The memory device 16 contains a program which the processor 14 accesses in order to control the valve(s), as described subsequently. In communication with the controller 12 is a volume controlling device 18. The volume controlling device 18 includes container(s) 20 housing fluid with which to rinse the slides. The fluid may contain Liquid Coverslip™ or wash buffer. The container(s) 20 is connected to valve(s) 22 which in turn are connected to a fluid reducing device 24 and a fluid application device 25. The fluid application device 25 applies fluid to the slide. For example, the fluid application device 25 may direct streams of rinse liquid over the portion of the slide where the biological sample is placed. Alternatively, the fluid application device may include a nozzle placed directly over the biological sample and simply drop fluid onto the biological sample.

The fluid valve(s) 22 are controlled by the processor 14 via fluid valve connections (not shown). There is a separate pair of wires (power and ground) for each valve, which are omitted for ease of display. Each valve, in the preferred embodiment, is an electromechanical valve which is activated by the processor 14. The processor 14 accesses the memory device 16 in order to determine the times in which to activate and deactivate the electromechanical valve.

The volume controlling device 18 includes a compressor 26 to pressurize the container(s) 20. The compressor 26 is connected to the container via a pressure line 28. The pressure line pressurizes the container(s) to 13 psi in a preferred embodiment so that when the valve(s) 22 are opened, the pressure is already on the line and the fluid may flow from the container to the valves via a line. The valve(s) determine whether the fluid is transferred to the fluid reducing device 24 via a fluid reducing line 29 or the fluid application device 25 via a fluid application line 31.

Figure 2A:
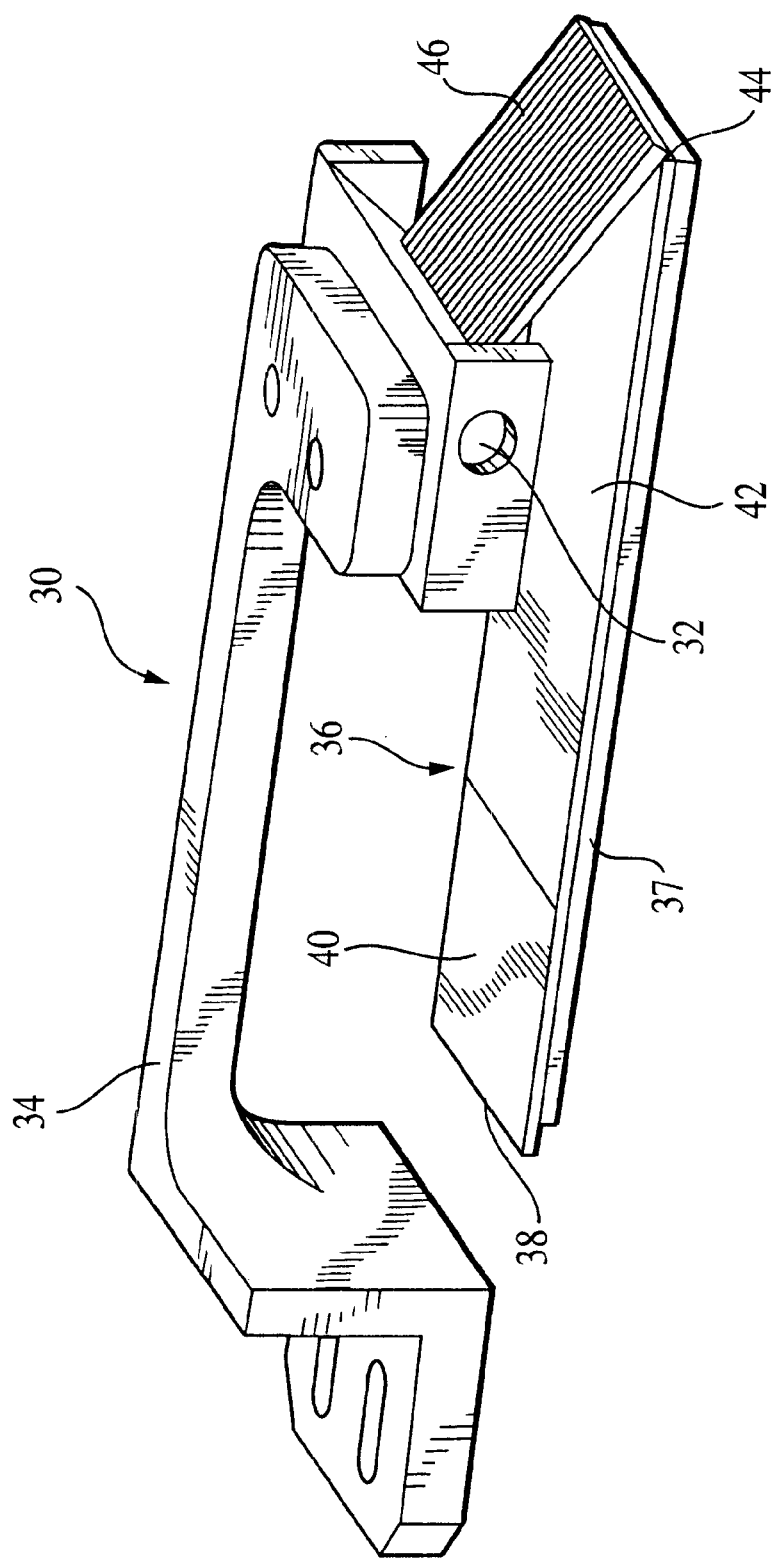
FIG. 2a is a perspective view of an example of a fluid reducing device as shown in FIG. 1.
Figure 2B:
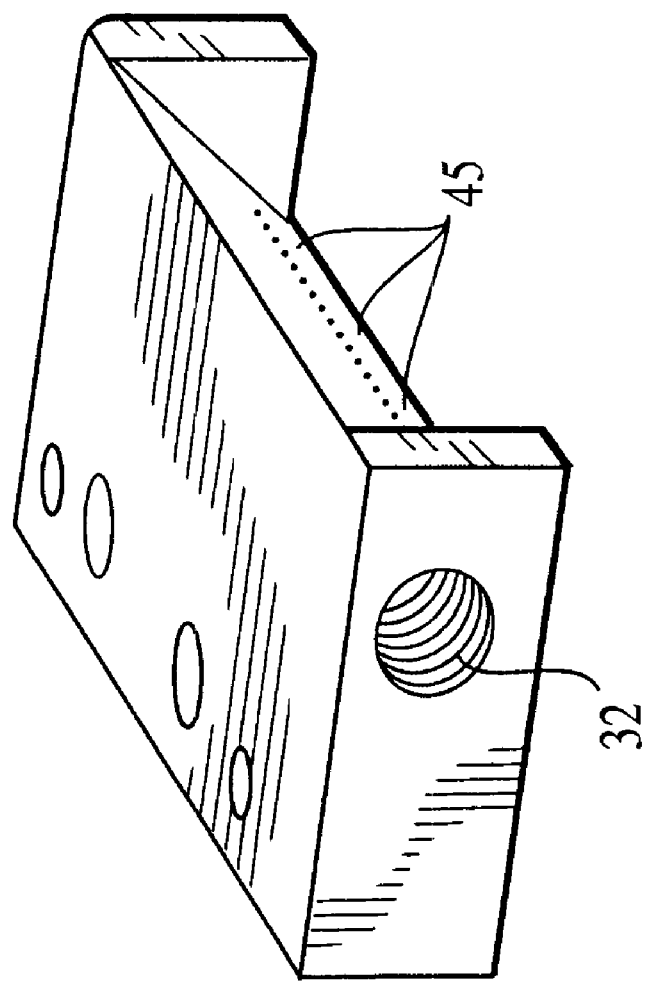

As discussed above, the valve(s) 22 are connected to the fluid reducing device 24. One example of a fluid reducing device 24 is a rinse device 30 as shown in FIGS. 2a and 2b. The rinse device 30 receives fluid via a connection 32 to the valve line. The rinse device 30 is also connected to the biological reaction apparatus via an arm 34. The rinse device 30 contains a plurality of openings by which fluid may flow. The fluid is directed onto a slide 36 which is sitting below the openings. The slide has one end 38 which is proximate to the apparatus, a portion which contains a barcode 40, a portion which contains the sample 42 and a second edge 44 which is distal to the apparatus. As shown in FIG. 2a, the streams of fluid 46 are directed to the distal end of the slide. The slide is placed on a mounting device 37 for holding the slide in place during processing. One example of a mounting device is to place the slide on posts.

The placement and direction of the fluid dictate whether the fluid is "pulling" the fluid from the slide. Because the fluid should not interfere with the biological sample, the fluid should be directed between the sample and an edge of the slide. In a preferred embodiment, the fluid is directed proximate, near or at an edge of the slide so that the sample is not disturbed. For example, the stream may be directed ⅛ inch from the edge of the slide. Any edge of the slide will suffice, but the edge furthest from the objects affixed to the slide is preferred (as shown in FIG. 2a, the fluid is directed toward the distal end 44). In addition, the direction of the fluid dictates whether the fluid is "pulling." In particular, the angle that the fluid make with the slide is less than 90°. In this manner, the directed fluid hits at, proximate to, or near the edge of the slide and washes off the edge of the slide. In a preferred embodiment, the angle of the stream is less than 45°, being approximately 20°. Thus, the action of the fluid stream acts to blow, aspirate or siphon fluid from previous treatments to the slide, such as a previous rinse.

The fluid reducing device 24 can send a single stream (in the form of a single pinpoint stream or in the form of a rectangular fan stream) or a plurality of streams (as shown in the rinse device 30 of FIG. 2a). In an alternate embodiment, separate streams are directed toward more than one edge of the slide simultaneously (e.g., directing one stream to the distal end and one stream to the proximal end of the slide).

In addition, the fluid sent from the fluid reducing device 24 may be liquid or air. In a preferred embodiment, liquid is used; however, for certain applications, as discussed subsequently, a gas may suffice. As shown in FIG. 2b, the rinse device 30 has a plurality of nozzles outlets or openings 45 which sends a plurality of streams 46 onto the distal edge of the slide 44.

The volume control subsystem accomplishes the goal of quickly controlling (in one embodiment reducing) the volume of fluid on a slide in two ways, with no impact to the affixed tissue. First, because the fluid from the fluid reducing device 24 is directed at a point or points toward an edge of the slide, the surface tension holding the fluid on the slide is broken at or along the point(s) on the edge of the slide where the fluid is directed. This provides a path of least resistance for the fluid on top of the slide to flow off the slide. Gravity alone is enough to draw fluid off a slide once the surface tension along an edge is broken. Gases and liquids passing through a nozzle outlet(s) or opening(s) 45 directed at, proximate to or near an edge can accomplish this goal.

Second, by using stream(s) of fluid along the edge, not only is the surface tension broken at that edge, but the surface tension between the similar fluids helps draw fluid off the slide. The similar fluids are attracted to each other, so as the jet stream(s) contact the volume of fluid on the slide, it is drawn off with the jet(s). In this manner, for better "drawing" of the liquid from the slide, the same type of liquid should be used in the stream of fluid. For example, if the slide is covered with wash buffer, wash buffer is sent in the stream(s) so that it can draw the wash buffer which is on top of the slide. Thus, in a preferred embodiment, liquid, rather than gas, should be output from the fluid reducing device. By using a liquid, the possibility of drying out the slide at the point of application is eliminated. The slide is thereafter left with a lower residual volume of fluid that covers as much of the slide as the original volume (i.e., no dry spots). In this manner, the apparatus reduces the aqueous volume while maintaining an aqueous film over the entire slide, thus keeping the slide and the tissue covered. Moreover, the biological sample on the slide is not disturbed since the fluid is simply pulled from atop the sample.

In addition, the apparatus produces consistent results such that the amount of fluid left on the slide after application of the stream(s) of fluid is reproducible. This reproducible amount left on the slide may be modified based upon certain parameters of the apparatus including without limitation: (1) the duration of the stream (i.e., the length of time the stream is directed to an edge of the slide); (2) the pressure of the stream; (3) the velocity of the stream; (4) the angle of the stream; (5) the distance of the stream from an edge on the slide (i.e., whether directly at the edge or near the edge); (6) the placement of the stream (i.e., the choice of which edge, either distal, proximal or either side edge; also the choice of which portion of an edge to direct the stream including the left, right, middle, or entire width of an edge); and (7) the composition of the stream (i.e., whether the nozzle is composed of a single round hole (for a single round stream), a plurality of holes (for a plurality of streams), or a rectangular outlet (for a continuous fan stream)). For example, the pressure may be modified by altering in the compressor the amount of pressure applied to the lines.

Figure 3A:
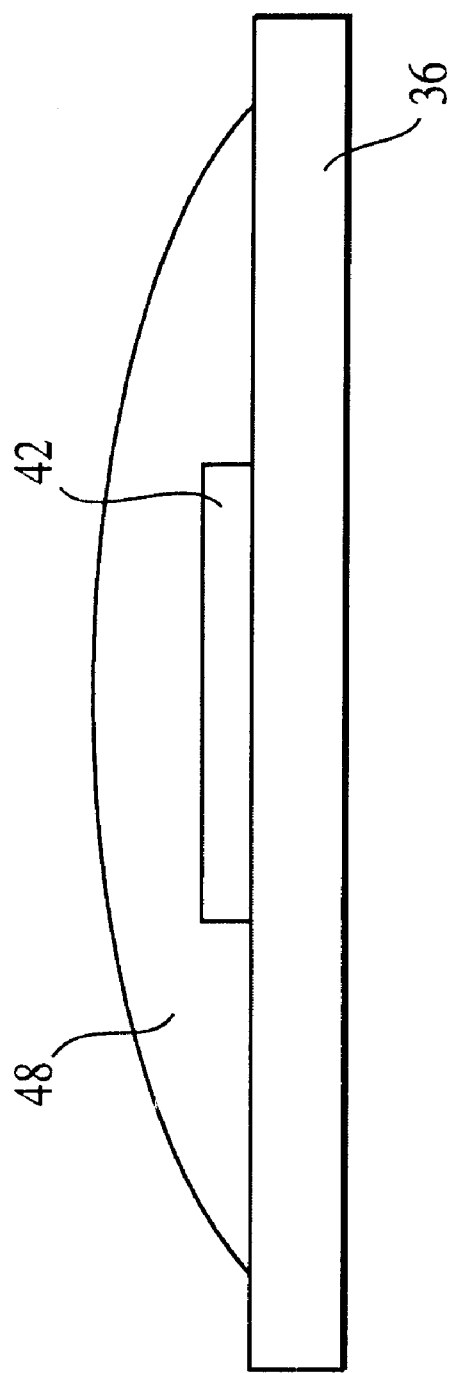
FIG. 3a is a side view of a slide prior to application of the slide aqueous volume reducing apparatus.
Figure 3B:
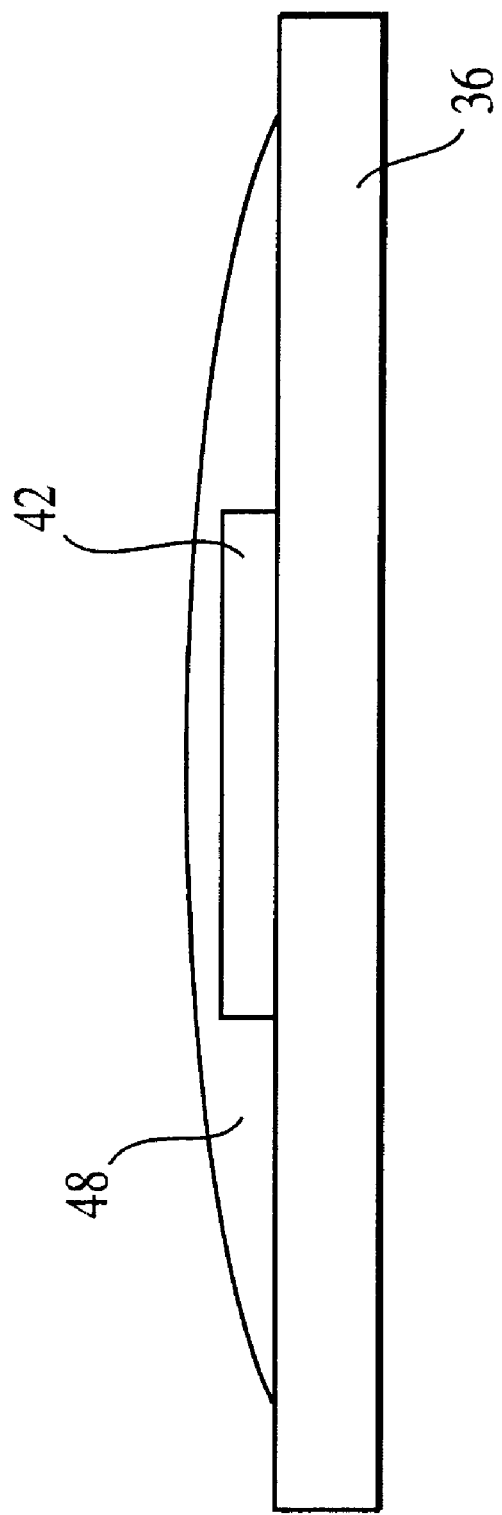
FIG. 3b is a side view of a slide after application of the slide aqueous volume reducing apparatus.

Referring to FIG. 2b, there is shown an expanded perspective view of a portion of the fluid reducing device in FIG. 2a. In the preferred embodiment, the fluid reducing device consists of 19 holes to be used as nozzle outlets (as shown in FIG. 2b), with each hole being 14 thousandths of an inch in diameter. The angle of the stream, as dictated by the nozzle outlets 45, is 20°. One example of the ability to control and reduce fluid volume is shown in FIGS. 3a and 3b. Prior to application of the apparatus, the fluid 48 on the slide is shown in FIG. 3a. After application of the apparatus, wherein fluid 48 is drawn from the top of the slide 36, the fluid volume on top of the slide is reduced to a consistent, reproducible amount. Specifically, after application of the apparatus, the volume of fluid remaining on the slide is the same, within certain tolerances, from machine to machine, regardless of the volume of fluid prior to application of the apparatus. For example, a slide may contain approximately 230–240 $\mu$L of wash buffer prior to application of the stream of fluid. And, after application of the stream of fluid in the preferred embodiment, the volume of fluid on the slide is consistently reduced to 100 $\mu$L.

In an alternate embodiment, the volume controlling device includes an object, such as an absorbent material, and an applicator. The applicator applies the absorbent material in contact to an edge of the slide to break the surface tension and draw fluid into it. The fluid being drawn into the material would also draw or pull the volume on the slide toward the edge. Thus, similar to sending stream(s) of fluid onto an edge of the slide, the absorbent material and applicator reduces the volume of fluid on top of the slide.

In still an alternate embodiment, the volume controlling device includes a vacuum to aspirate the liquid off the slide. The vacuum is placed at an edge of the slide, and similar to sending stream(s) of fluid, breaks the surface tension and pulls fluid toward the edge of the slide.

Although certain presently preferred embodiments of the invention have been described herein, it will be apparent to those skilled in the art to which the invention pertains that variations and modifications of the described embodiment may be made without departing from the spirit and scope of the invention. Accordingly, it is intended that the invention be limited only to the extent required by the appended claims and the applicable rules of law.

What is claimed is:

1. A method for rinsing a slide having a biological sample positioned on an upper surface of the slide, the method comprising the steps of:

applying a layer of liquid onto the upper surface of the slide so as to cover the biological sample with the liquid; and directing at least one stream of fluid in order to pull from the slide at least a portion of the liquid applied to the upper surface, wherein the step of directing at least one stream of fluid includes directing at least one stream of fluid on said slide surface between the biological sample and the edge of the slide, the at least one stream of fluid making an angle with the slide of less than 90 degrees.

2. The method of claim 1 wherein the at least one stream of the fluid is directed proximate to the edge of the slide.

3. The method of claim 1 wherein a distal end of the slide is farthest from the biological sample and wherein the at least one stream of fluid is directed to the distal end.

4. The method of claim 1 wherein the step of directing at least one stream of fluid in order to pull from the slide at least a portion of the liquid includes breaking a surface tension at an edge of the slide so as to pull at least a portion of the liquid from the slide.

5. The method of claim 4 wherein breaking a surface tension at an edge of the slide includes directing a stream of the fluid proximate to the edge of the slide.

6. The method of claim 1 wherein the step of removing at least a portion of the fluid includes directing a stream of the fluid at or proximate to the edge of the slide, the stream of the fluid making an angle with the slide of less than 90°.

7. The method of claim 1, wherein the liquid applied on the upper surface of the slide is the same type as the fluid directed in the stream, and wherein the step of directing at least one stream of fluid in order to pull from the slide at least a portion of the liquid includes creating surface tension between at least a portion of the liquid directed in the stream and at least a portion of the liquid on the upper surface of the slide in order to pull the at least a portion of the liquid on the upper surface from the slide.

8. The method of claim 1, wherein the at least one stream of fluid is directed to a distal end of the slide.

9. A method for rinsing a slide having a biological sample positioned on an upper surface of the slide, the method comprising the steps of:

applying a layer of liquid onto the upper surface of the slide so as to cover the biological sample with the liquid; and directing at least one stream of fluid onto the slide with the fluid falling off an end of the slide, the stream of fluid being directed on said slide surface between the biological sample and the end of the slide so as to remove at least a portion of the liquid on the upper surface of the slide, the at least one stream of fluid making an angle with the slide of less than 90 degrees.

10. The method of claim 9 wherein the at least one stream of fluid is directed proximate to the end of the slide.

11. The method of claim 10 wherein the at least one stream of fluid includes a plurality of streams of fluid.

12. The method of claim 9 wherein the at least one stream of fluid includes at least one stream of the liquid which was applied during the step of applying a layer of liquid onto the upper surface of the slide.

13. The method of claim 9, wherein the liquid applied on the upper surface of the slide is the same type as the liquid directed in the stream, and wherein the step of directing at least one stream of fluid onto the slide includes creating surface tension between at least a portion of the liquid directed in the stream and at least a portion of the liquid on the upper surface of the slide in order to pull the at least a portion of the liquid on the upper surface from the slide.

* * * * *